US006278786B1

United States Patent
McIntosh

(10) Patent No.: US 6,278,786 B1
(45) Date of Patent: Aug. 21, 2001

(54) ACTIVE NOISE CANCELLATION AIRCRAFT HEADSET SYSTEM

(75) Inventor: Jason D. McIntosh, Weston, FL (US)

(73) Assignee: Telex Communications, Inc., Minneapolis, MN (US)

( * ) Notice: Subject to any disclaimer, the term of this patent is extended or adjusted under 35 U.S.C. 154(b) by 0 days.

(21) Appl. No.: 09/124,686

(22) Filed: Jul. 29, 1998

Related U.S. Application Data

(60) Provisional application No. 60/054,106, filed on Jul. 29, 1997.

(51) Int. Cl.[7] .......................... A61F 11/06; G01K 11/16; H03B 29/00
(52) U.S. Cl. .................. 381/71.6; 381/71.13; 381/71.14; 381/72; 381/94.2
(58) Field of Search ................................. 381/71.1, 71.2, 381/71.3, 71.4, 71.5, 71.6, 71.7, 71.8, 71.9, 71.11, 71.12, 71.13, 71.14, 94.1, 94.2, 94.3, 94.7, 94.8, 94.9, 72, 73.1, FOR 123, FOR 124; 708/322

(56) References Cited

U.S. PATENT DOCUMENTS

| | | | |
|---|---|---|---|
| 3,729,598 | 4/1973 | Tegt et al. | 179/175.1 A |
| 4,135,143 | 1/1979 | Argentieri et al. | 340/27 R |

(List continued on next page.)

FOREIGN PATENT DOCUMENTS

| | | | |
|---|---|---|---|
| 2265790 | * 10/1993 | (GB) | 381/73.1 |
| 92-05538 | * 4/1992 | (WO) | 381/FOR 123 |

OTHER PUBLICATIONS

Brochure entitled "Telex Technical Data–Airman ANR(TM) 200—Active Noise Reduction Headset"; Telex Communications, Inc., 9600 Aldrich Avenue South, Minneapolis, MN 55420 USA; Jul. 1994, 2 pages.

Brochure entitled "Telex ANR(TM) Noise Reduction Headset System", Telex Communications, Inc., 9600 Aldrich Avenue South, Minneapolis, MN 55420 USA; 1990; 4 pages.

*Primary Examiner*—Xu Mei
(74) *Attorney, Agent, or Firm*—Fredrikson & Byron, P.A.

(57) ABSTRACT

An active noise cancellation aircraft headset system. A speaker is mounted within each earcup of a headset for receiving and acoustically transducing a composite noise cancellation signal. A microphone is also mounted within each earcup for transducing acoustic pressure within the earcup to a corresponding analog error signal. An analog filter receives the analog error signal and inverts it to generate an analog broadband noise cancellation signal. The analog error signal is also provided to an analog to digital converter, which receives the analog microphone error signal and converts it to a digital error signal. A DSP takes the digital error signal and, using an adaptive digital feedback filter, generates a digital tonal noise cancellation signal. A digital to analog converter then converts the digital tonal noise cancellation signal to an analog tonal noise cancellation signal so that it can be combined with the analog broadband noise cancellation signal. The resultant composite cancellation signal is provided to the speakers in the earcups to cancel noise within the earcups. The broadband analog cancellation is effective to reduce overall noise within the earcup, and the DSP not only provides active control of the analog cancellation loop gain to maximize the effectiveness of the broadband analog cancellation but also uses the adaptive feedback filter/algorithm to substantially reduce at least the loudest tonal noises penetrating the earcup, including engine and propeller noises, as well as harmonic vibrations of components of the aircraft's fuselage.

10 Claims, 7 Drawing Sheets

U.S. PATENT DOCUMENTS

| | | | |
|---|---|---|---|
| 4,355,294 | 10/1982 | Ben-David et al. | 340/27 R |
| 4,473,906 | 9/1984 | Warnaka et al. | 381/71 |
| 4,494,074 | 1/1985 | Bose | 330/109 |
| 4,562,589 | 12/1985 | Warnaka et al. | 381/71 |
| 4,644,581 | 2/1987 | Sapiejewski | 381/74 |
| 4,654,871 | 3/1987 | Chaplin et al. | 381/72 |
| 4,677,677 | 6/1987 | Eriksson | 381/71 |
| 4,689,821 | 8/1987 | Salikuddin et al. | 381/71 |
| 4,736,431 | 4/1988 | Allie et al. | 381/71 |
| 4,862,506 | 8/1989 | Landgarten et al. | 381/71 |
| 4,878,188 | 10/1989 | Ziegler, Jr. | 364/724.01 |
| 4,922,542 | 5/1990 | Sapiejewski | 381/187 |
| 4,953,217 | 8/1990 | Twiney et al. | 381/72 |
| 5,046,103 | 9/1991 | Warnaka et al. | 381/71 |
| 5,105,377 | 4/1992 | Ziegler, Jr. | 364/724.01 |
| 5,126,681 | 6/1992 | Ziegler, Jr. et al. | 328/165 |
| 5,181,252 | 1/1993 | Sapiejewski et al. | 381/187 |
| 5,182,774 | 1/1993 | Bourk | 381/71 |
| 5,305,387 | 4/1994 | Sapiejewski | 381/71 |
| 5,311,453 | 5/1994 | Denenberg et al. | 364/574 |
| 5,317,273 | 5/1994 | Hanson et al. | 324/616 |
| 5,361,303 | 11/1994 | Eatwell | 381/71 |
| 5,361,304 | 11/1994 | Jones et al. | 381/72 |
| 5,375,174 | 12/1994 | Denenberg | 381/71 |
| 5,400,406 | 3/1995 | Heline, Jr. et al. | 381/58 |
| 5,402,497 | 3/1995 | Nishimoto et al. | 381/95 |
| 5,416,845 | 5/1995 | Shen | 381/71 |
| 5,418,857 | 5/1995 | Eatwell | 381/71 |
| 5,425,105 | 6/1995 | Lo et al. | 381/71 |
| 5,436,933 | 7/1995 | Andruzzi, Jr. | 375/345 |
| 5,440,642 | 8/1995 | Denenberg et al. | 381/71 |
| 5,452,361 | 9/1995 | Jones | 381/71 |
| 5,481,615 | 1/1996 | Eatwell et al. | 381/71 |
| 5,546,467 | 8/1996 | Denenberg | 381/71 |
| 5,559,893 | 9/1996 | Krokstad et al. | 381/71 |
| 5,563,817 | 10/1996 | Ziegler, Jr. et al. | 364/724.19 |
| 5,577,511 | 11/1996 | Killion | 128/746 |
| 5,600,072 * | 2/1997 | Darlington et al. | 381/72 |
| 5,604,813 | 2/1997 | Evans et al. | 381/71 |
| 5,610,987 | 3/1997 | Harley | 381/67 |
| 5,638,022 | 6/1997 | Eatwell | 327/551 |
| 5,638,454 | 6/1997 | Jones et al. | 381/71 |
| 5,652,799 | 7/1997 | Ross et al. | 381/71.11 |
| 5,815,582 * | 9/1998 | Claybaugh et al. | 381/72 |
| 5,853,667 * | 12/1998 | Pan et al. | 381/71.6 |

* cited by examiner

ACTIVE NOISE CANCELLATION AIRCRAFT HEADSET SYSTEM

RELATED APPLICATIONS

This application is a continuation-in-part of provisional application Ser. No. 60/054,106, filed Jul. 29, 1997, the contents of which are hereby incorporated by reference.

TECHNICAL FIELD

The invention relates to devices and methods for active noise cancellation, and, in particular, to an aircraft headset system having active noise cancellation capabilities.

BACKGROUND OF THE INVENTION

Cabin noise in small aircraft is a combination of noise from a variety of sources, the major ones being the engine, wind, and propeller (propellers are noisier on multi-engine planes where the propellers are close to the wing—noise is generated each time a prop blade passes the leading edge of the aircraft wing). Such aircraft cabin is sufficiently loud that small plane pilots routinely wear noise attenuating headsets. Such headsets usually employ passive noise attenuation in the form of an annular cushion carried on the rim of each earcup. The cushion is sufficiently flexible to conform to the pilot's head, thereby creating an acoustical seal around the pilot's ear. Such passive noise attenuation headsets—frequently referred to as circumaural headsets—can be quite effective for higher frequencies (e.g., above about 500 Hz), but typically are much less effective at lower frequencies.

Analog active noise cancellation headsets have been commercialized to reduce the noise level within headset earcups. Examples of such headsets can be found, e.g., in U.S. Pat. Nos. 5,182,774, 4,953,217 and 4,644,581. These analog systems utilize a noise detection microphone (sometimes referred to as an "error microphone") mounted within the earcup. The noise signal detected by the microphone is provided to an inverter which generates a noise cancellation signal provided to the speaker in the earcup. The acoustical pressure in the earcup is then the sum of the external noise that has penetrated the earcup and the acoustical output of the speaker. The speaker output, thus, is intended to exactly cancel the noise. Additional radio, intercom or other desired signals may also be provided to the speaker, as desired.

Commercial implementations of such analog systems have generally been capable of reducing noise by about 10–15 dB for frequencies of up to about 500 Hz, the range in which noise cancellation is most needed. These noise reductions systems have the advantage of being effective for random, unpredictable noises, as well as broadband noise (such as wind noise) but generally are capable of only about 10–15 dB of reduction. Attempts to make larger reductions require increasing the gain of the cancellation signal, and generally result in instabilities (best solved by reducing the feedback loop gain). While such broadband noise reduction is helpful, as can be seen from FIG. 1, the loudest noises in the low frequency range of a typical small plane cabin, even if attenuated by 10–15 dB, are still very loud.

Digital signal processor (DSP) based adaptive feedback cancellation systems have been proposed for dealing with certain kinds of noise that, though not necessarily constant are predictable. In these systems, an algorithm is used to construct, in real time, an adaptive filter which is used to generate the noise cancellation signal. In applications where these systems have been successfully employed the predictive nature of a tone has enabled such systems to achieve very significant levels of noise reduction—as much as 60 dB. While such dramatic noise reductions are possible, these systems typically are not sufficiently responsive to deal with transient or random noises. Rather, their effectiveness is dependent on the existence of a relatively predictable noise, such as is found in tonal noise, to which the system can adapt and make generally accurate predictions (hence, the word "adaptive"). Thus, the effectiveness of these systems is also constrained to a narrow bandwidth—i.e., they generally work well only on tonal noises which, by definition, have a narrow bandwidth (see, e.g., U.S. Pat. No. 5,546,467, showing use of a DSP active noise cancellation system to cancel a narrow noise band at about 400 Hz, produced by the fan of a hair dryer).

SUMMARY OF THE INVENTION

FIG. 1 illustrates that the loudest noises in many small aircraft are attributable to engine and prop noise, as well as other harmonic vibrations in the fuselage, which are tonal in nature. That is, they are generated by the regular and repetitive movements of the engine, propellers or fuselage components. Consequently, most of the noise attributable to these sources is concentrated in a few relatively narrow low frequency bands. Applicant has discovered that, by combining analog and digital noise cancellation techniques a very effective noise cancellation headset system can be produced. Moreover, the DSP utilized in the system can also be employed to monitor the analog cancellation, providing active control of the gain of the analog cancellation signal to maximize the effectiveness of the broadband analog cancellation component of the cancellation signal.

The invention provides an active noise cancellation aircraft headset system which includes a headset of the type having a headband and a pair of earcups mounted to the headband. A speaker is mounted within each of the earcup for receiving and acoustically transducing a composite noise cancellation signal, and a microphone is also mounted within each earcup for transducing acoustic pressure within the earcup to a corresponding analog error signal. An analog filter receives the analog error signal and inverts it to generate an analog broadband noise cancellation signal. The analog error signal is also provided to an analog to digital converter, which receives the analog microphone error signal and converts it to a digital error signal. A DSP takes the digital error signal and, using an adaptive digital feedback filter, generates a digital tonal noise cancellation signal. A digital to analog converter then converts the digital tonal noise cancellation signal to an analog tonal noise cancellation signal so that it can be combined with the analog broadband noise cancellation signal. The resultant composite cancellation signal is provided to the speakers in the earcups to cancel noise within the earcups. The broadband analog cancellation is effective to reduce overall noise within the earcup, and the DSP not only provides active control of the analog cancellation loop gain to maximize the effectiveness of the broadband analog cancellation but also uses the adaptive feedback filter/algorithm to substantially reduce at least the loudest tonal noises penetrating the earcup (such tonal noises being engine and propeller noises, and harmonic vibrations of fuselage components).

DETAILED DESCRIPTION OF THE INVENTION

Figure 1:
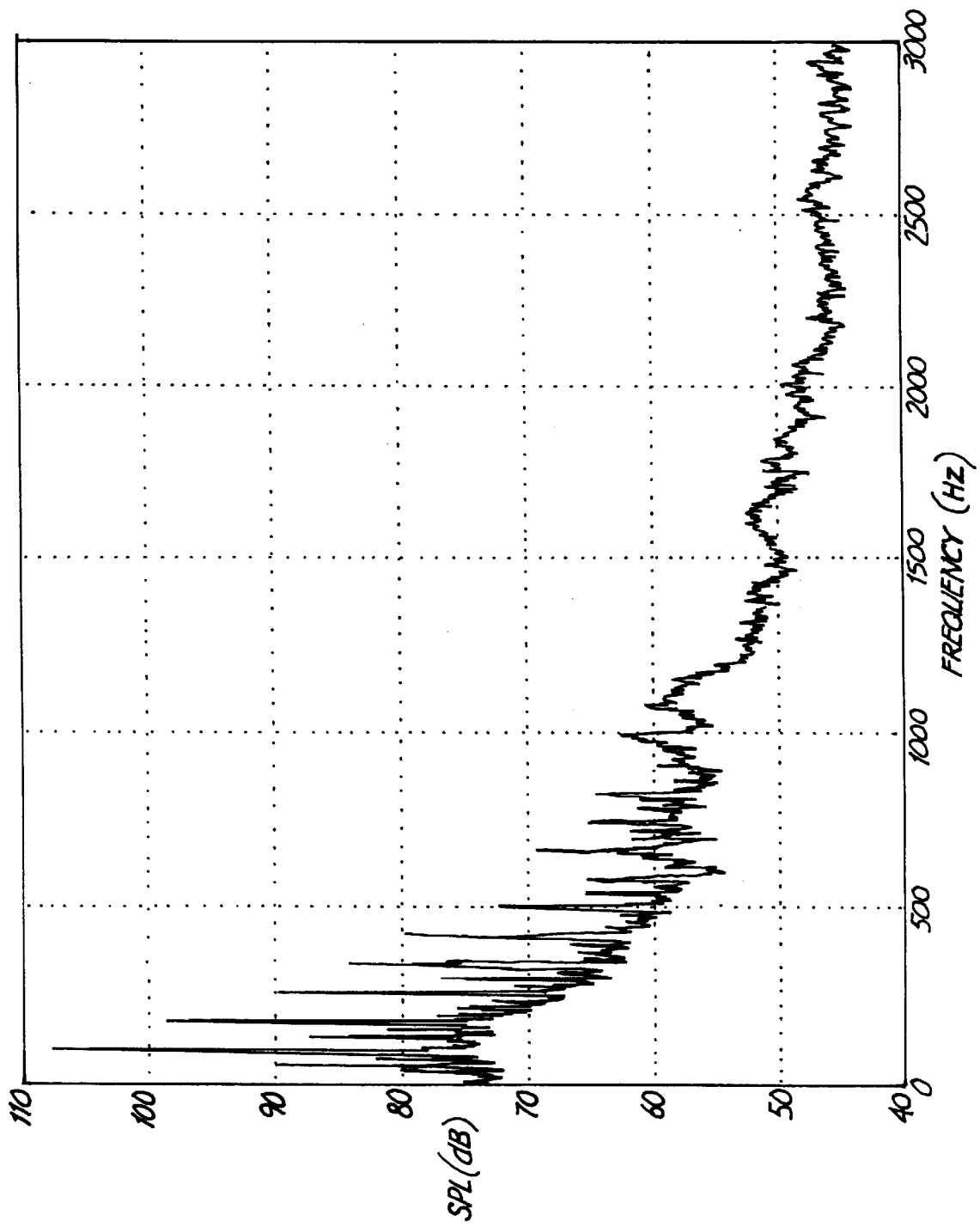
FIG. 1 is a graph illustrating the sound pressure level ("SPL") in the cabin of an airplane.
Figure 2:
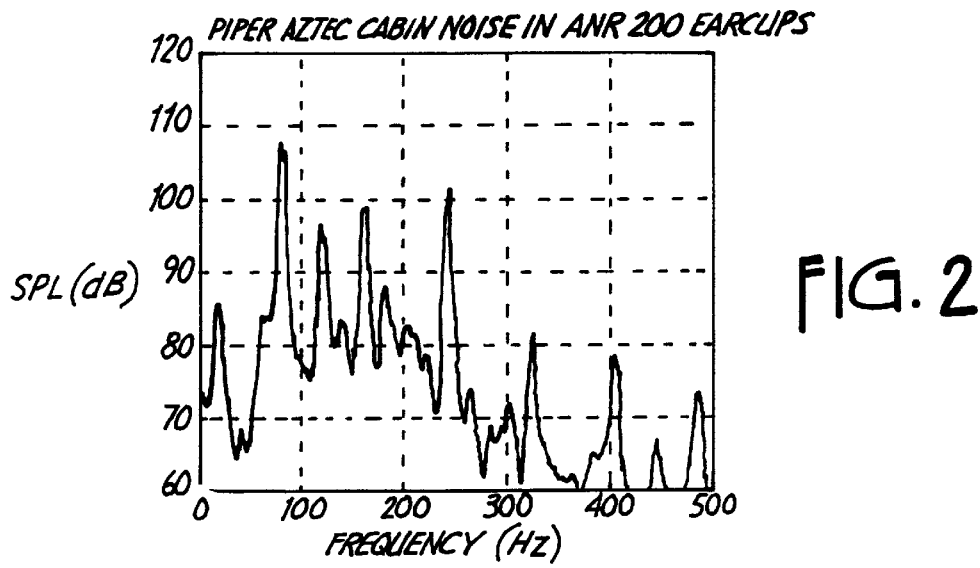
FIG. 2 is a graph illustrating the sound pressure level within the earcup of a passive noise attenuating headset.

FIG. 1 is a graph illustrating the sound pressure level (SPL) in the cabin of a Piper Aztec airplane. As can be seen from this graph, the SPL at frequencies below about 500 Hz are quite high. FIG. 2 shows the SPL, for frequencies up to 500 Hz, measured within the earcup of a typical circumaural headset. This figure illustrates the fact that the passive noise attenuation afforded by the headset is not very significant below 500 Hz.

Figure 3:
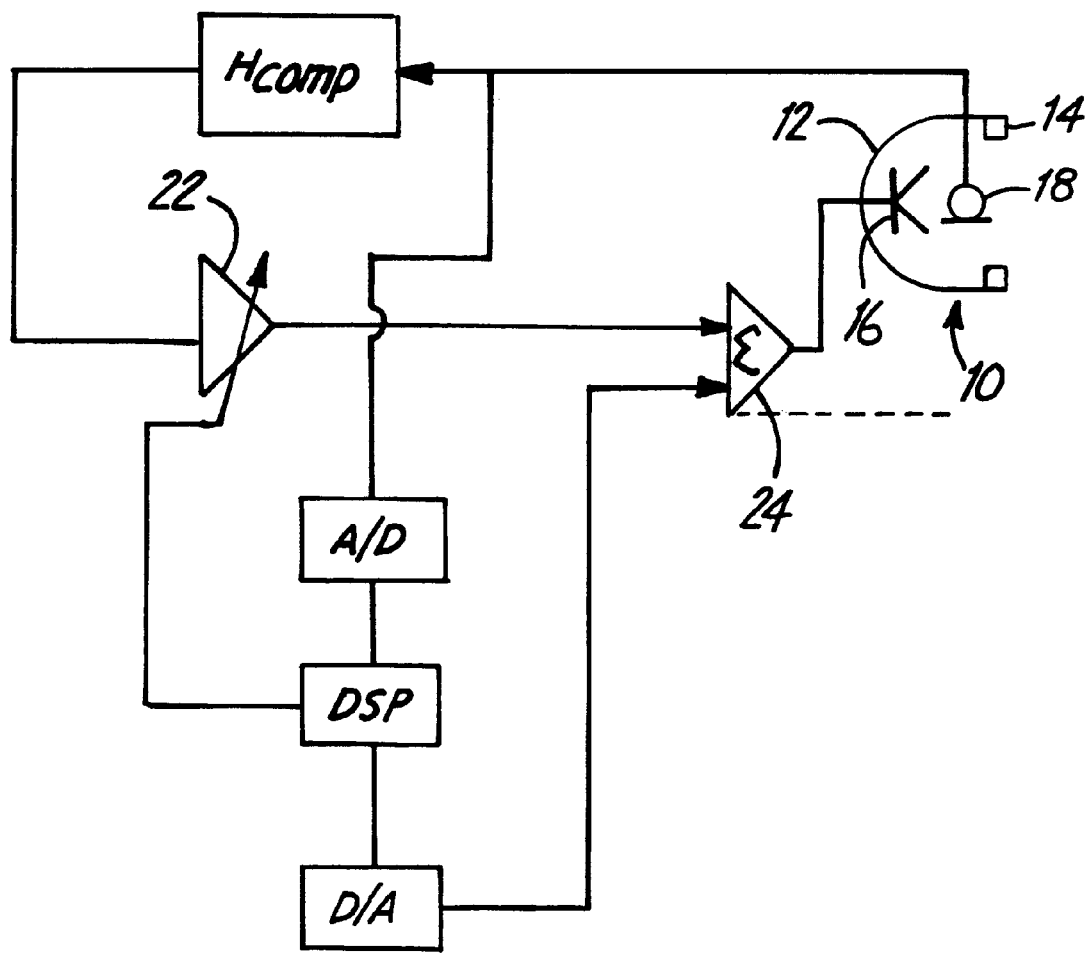
FIG. 3 is a schematic diagram of a noise cancellation circuit for a single channel headset system of the invention.

FIG. 3 depicts the essential elements of a headset system of the invention, providing both analog broadband noise cancellation and digital adaptive tonal noise cancellation. A headset 10 includes an earcup 12 carrying a conventional circumaural cushion 14, a conventional speaker element 16 and an error microphone 18 mounted within the earcup 12. External sounds penetrating the earcup 12 are detected by the error microphone 18, which transduces the sounds (i.e., the acoustic pressure) to a corresponding analog error signal. The error signal is provided to a conventional (nonadaptive) compensation filter $H_{comp}$, which receives the analog error signal and inverts it to generate an analog broadband noise cancellation signal. This cancellation signal is amplified by a variable gain amplifier 22, and the amplified analog cancellation signal is then provided to summing amplifier 24, the output of which drives the speaker 16 to cancel external noise which has penetrated the earcup 12.

The analog error signal from the microphone is also provided to a DSP through a suitable A/D converter. The DSP utilizes an adaptive feedback filter to generate a digital tonal noise cancellation signal which is converted by a suitable D/A converter to an analog tonal noise cancellation signal. The tonal noise cancellation signal is then provided to the summing amplifier 24, where it is combined with the broadband analog cancellation signal to form a composite cancellation signal. The composite cancellation signal is used to drive the speaker 16 to at least partially cancel aircraft noise which has penetrated the earcup 12.

Figure 4:
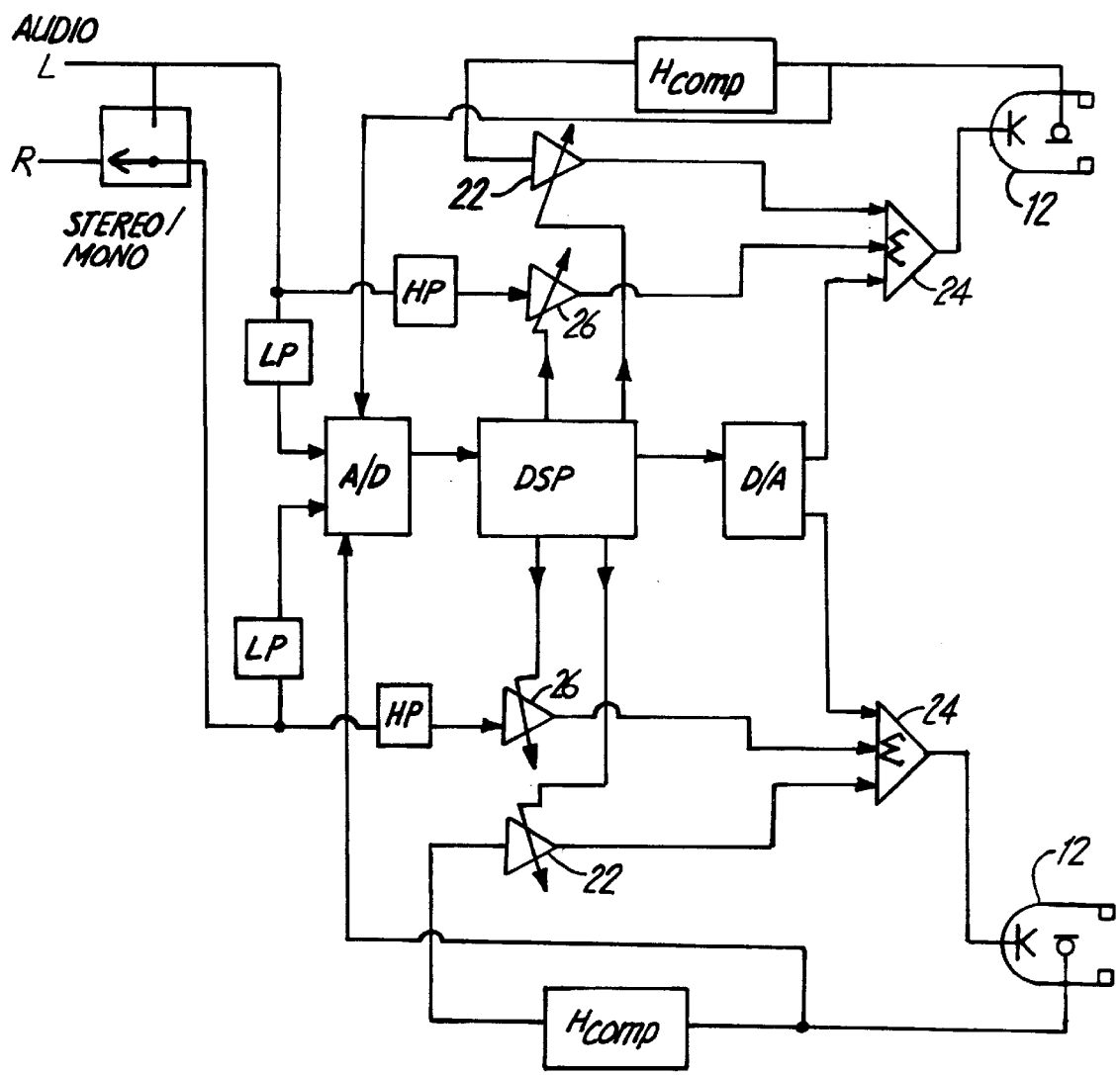
FIG. 4 is a schematic diagram of a noise cancellation circuit for a stereo headset system of the invention, with audio inputs.

FIG. 4 illustrates implementation of the system when adding an audio signal (such as the aircraft radio communication signal). The essential elements of the system are repeated for the left and right channels, providing discrete signals to the left and right speakers of the headset, except that the DSP and the A/D and D/A converters are shared. Also, high pass HP and low pass LP filters are provided in the audio signal for each channel; the low frequencies pass through the DSP and are equalized (so that the system does not cancel them when they are acoustically reproduced by the speakers in the earcups), while the high frequencies pass directly to the summing amp 24 by way of a DSP-controlled gain stage 26 which permits loudness control by the DSP (as is described below).

The adaptive digital feedback filter may be any suitable adaptive filter known in the art; e.g., applicant has successfully demonstrated the effectiveness of the adaptive feedback ANC system described in S. Kuo & D. Morgan, *Active Noise Control Systems—Algorithms and DSP Implementations*, p. 195–200 (John Wiley & Sons, Inc., 1996). That system is a regenerative feedback filtered-x-least-means-square (FXLMS) algorithm. As described in this reference, the system can be viewed as an adaptive feedforward system that, in effect, synthesizes or regenerates its own reference signal based only on the adaptive filter output and the error signal.

Figure 5:
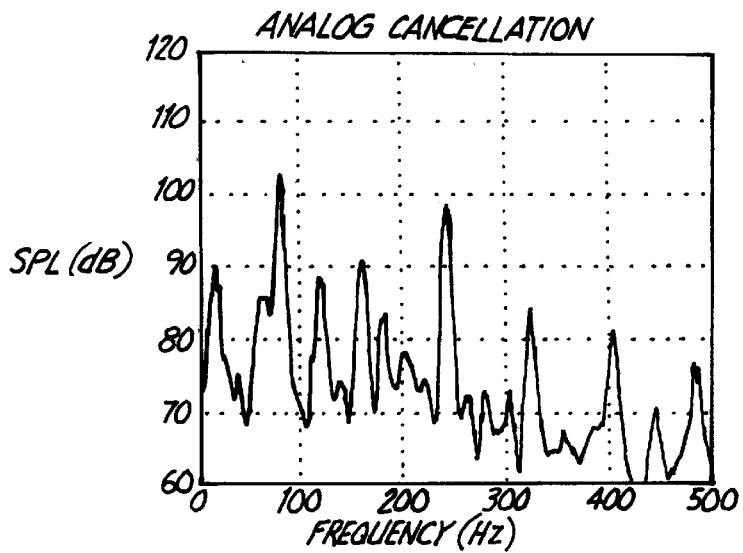
FIG. 5 is a graph illustrating the sound pressure level within the earcup of the headset utilized in the graph of FIG. 2, but with analog cancellation being employed.
Figure 6:
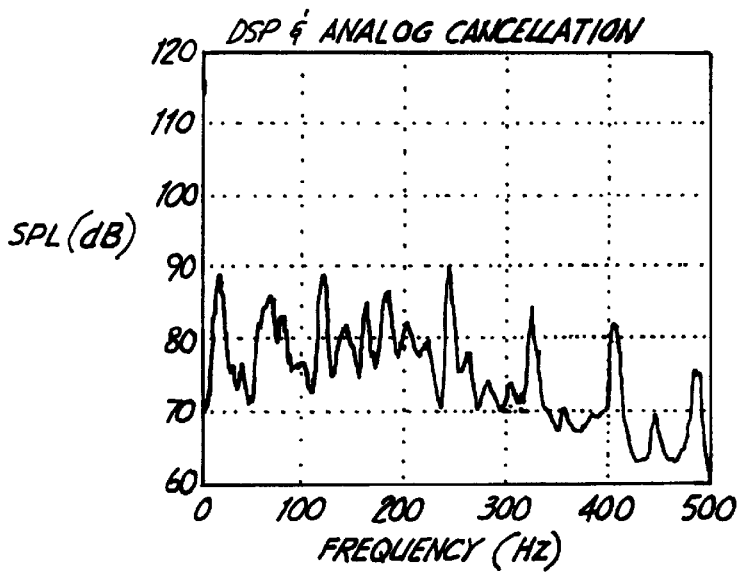
FIG. 6 is a graph illustrating the sound pressure level within the earcup of the headset utilized in the graphs of FIGS. 2 and 5, but with the combined DSP and analog cancellation of the invention being employed.

To demonstrate the effectiveness of the system of the invention, applicant utilized a Telex ANR 200 headset having analog noise cancellation, and adapted the headset to incorporate the Kuo & Morgan digital adaptive feedback filter mentioned above with a normalized step size and a leaky update on a Pentium® 133 PC. The A/D converter was an 8 channel WaveBook from IOtech connected to a parallel port; the D/A converter was an 8 channel ISA card from Industrial Computer Source, model AOB8/12; anti-aliasing and anti-imaging filters utilized were $4_{th}$ order Sallen-Keys low pass filters, $f_o$=460 Hz; sampling frequency was 1300 Hz; 50 FIR filter taps were utilized, with a step size of 0.005 and a leak of 0.99998. Tests were performed with the headset mounted on a simulated head placed about three feet in front of a JBL™ Studio Monitor 4412, and aircraft cabin noise was played through the speaker. The aircraft noise was measured in an actual aircraft cabin with a ½" B&K microphone and recorded onto digital audio tape. FIG. 5 depicts the sound pressure levels measured with only the analog system functional. Although the analog system does reduce the maximum sound levels somewhat, the tallest peak is still over 100 dB. FIG. 6 shows the effectiveness of adding the adaptive DSP cancellation. With this combination of techniques, none of the frequencies exceed 90 dB, and the tallest peaks in FIGS. 2 and 5 have been reduced by over 20 dB. Comparison of FIGS. 5 and 6 shows an increase in the broadband noise; this was attributed to the DSP filter, which essentially adapts to a comb filter passing only the tonal components. For FIR filters, the sharpness of the filters (their Q) is directly related to the length of the filter, and, therefore, the number of filter taps. Increasing the number of taps improves the filter sharpness and, hence, reduces the increase to the broadband noise. The number of filters, however, must be balanced with convergence time, as a larger filter will yield better steady state control but will take longer to achieve it and will be less responsive to changes in the tonal noise being cancelled.

While the above-described data and demonstration was performed on a PC, preferably the system of the invention is executed utilizing a suitable DSP, such as Analog Devices ADSP2106 DSP.

In addition to generating the digital tonal noise cancellation signal, the DSP also desirably is utilized to monitor the microphone error signal and control the gain of the variable gain amplifier 22 to maximize the effectiveness of the analog noise cancellation signal. As is discussed above, nonadaptive analog noise reduction systems can suffer from instabilities. The simplest strategy for dealing with this problem is to decrease the feedback loop gain so that stability is realized for all operating conditions. This results in much poorer performance under actual in-use flight conditions. The DSP, however, can be utilized to monitor the analog filter's stability condition and increase the loop gain until the system is on the verge of instability, thus obtaining maximum noise reduction from the non-adaptive analog component of the system under all conditions.

Figure 7:
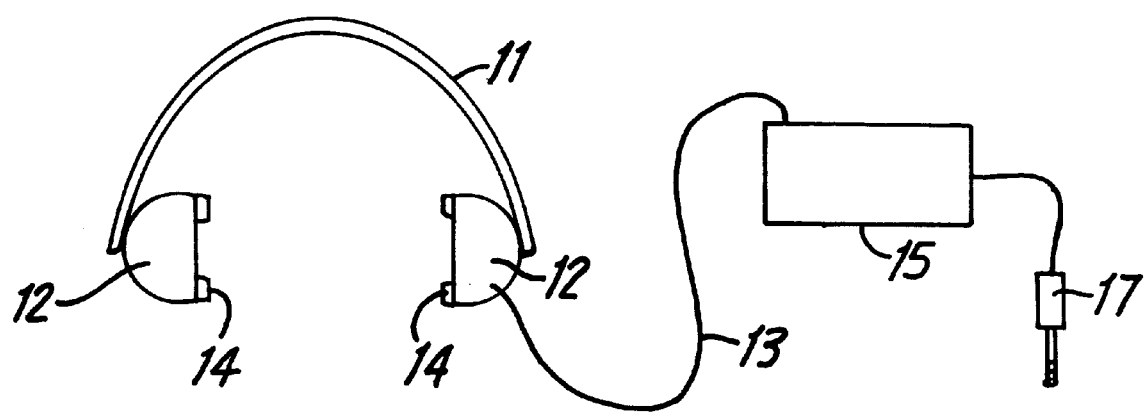
FIG. 7 figuratively illustrates one implementation of a headset system of the invention.

In one embodiment of the invention the entire headset system is implemented in a headset having an integrated electronic control system. FIG. 7 figuratively illustrates such a headset, having a pair of earcups 12 connected by a headband 11. The earcups are connected by a cord 13 to a housing 15, which typically houses batteries for powering the DSP and associated electronics. The DSP and electronics may, if desired, be incorporated into the earcups 12 or the headband 11, but preferably are disposed within the housing 15. Each earcup has its own speaker, error microphone, and set of associated electronics as illustrated in FIG. 4, though the DSP as well as the A/D and D/A converters may be shared and need not be duplicated (a manual stereo/mono switch may also be provided, or stereo/mono control may be provided electronically through the DSP as is described below). If desired, each earcup could employ two speakers, one transducing the noise cancellation signal and the other transducing the aircraft radio (and/or other desired audio signals). Another cord, terminating in a conventional plug 17, connects the housing 15 (and, thus, the entire system) to the radio jack in the aircraft.

Figure 8:
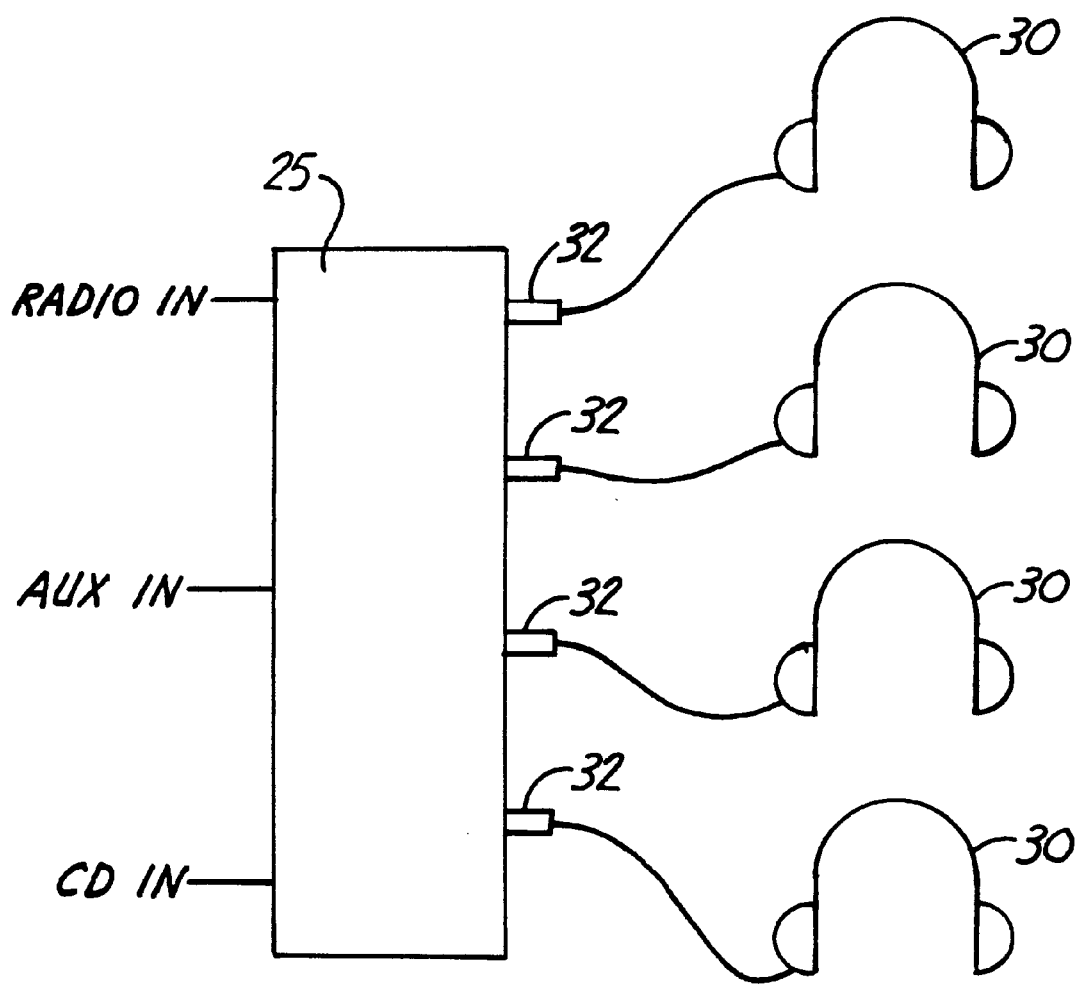
FIG. 8 figuratively illustrates a second implementation of a headset system of the invention.

In another embodiment of the invention, the power of the DSP unit is utilized to supply signal processing for multiple matched headsets. FIG. 8 figuratively illustrates a portable aircraft intercom system comprised of a housing 25 which houses much of the electronics, including the DSP unit and, desirably, batteries for powering the system. A number of headsets 30 (four of them being depicted in the drawing) can be plugged into the housing 25 by means of conventional plugs 32. Each of the headsets 30 has its own earcup speakers and error microphones. Other electronic components, such as the summing amplifiers, analog cancellation filters, A/D and D/A converters, etc., can be located either in each of the respective headsets or in the housing, but preferably are located in the housing. By sharing the DSP unit among several headsets, costs for a multiple user system can be reduced while all users enjoy the benefits of the noise reduction ability of the system. The housing 25 includes a port for the aircraft radio signal, and has additional inputs allowing, e.g., a CD player or the signal from other auxiliary input devices to be heard by the pilot and passengers.

Figure 9:
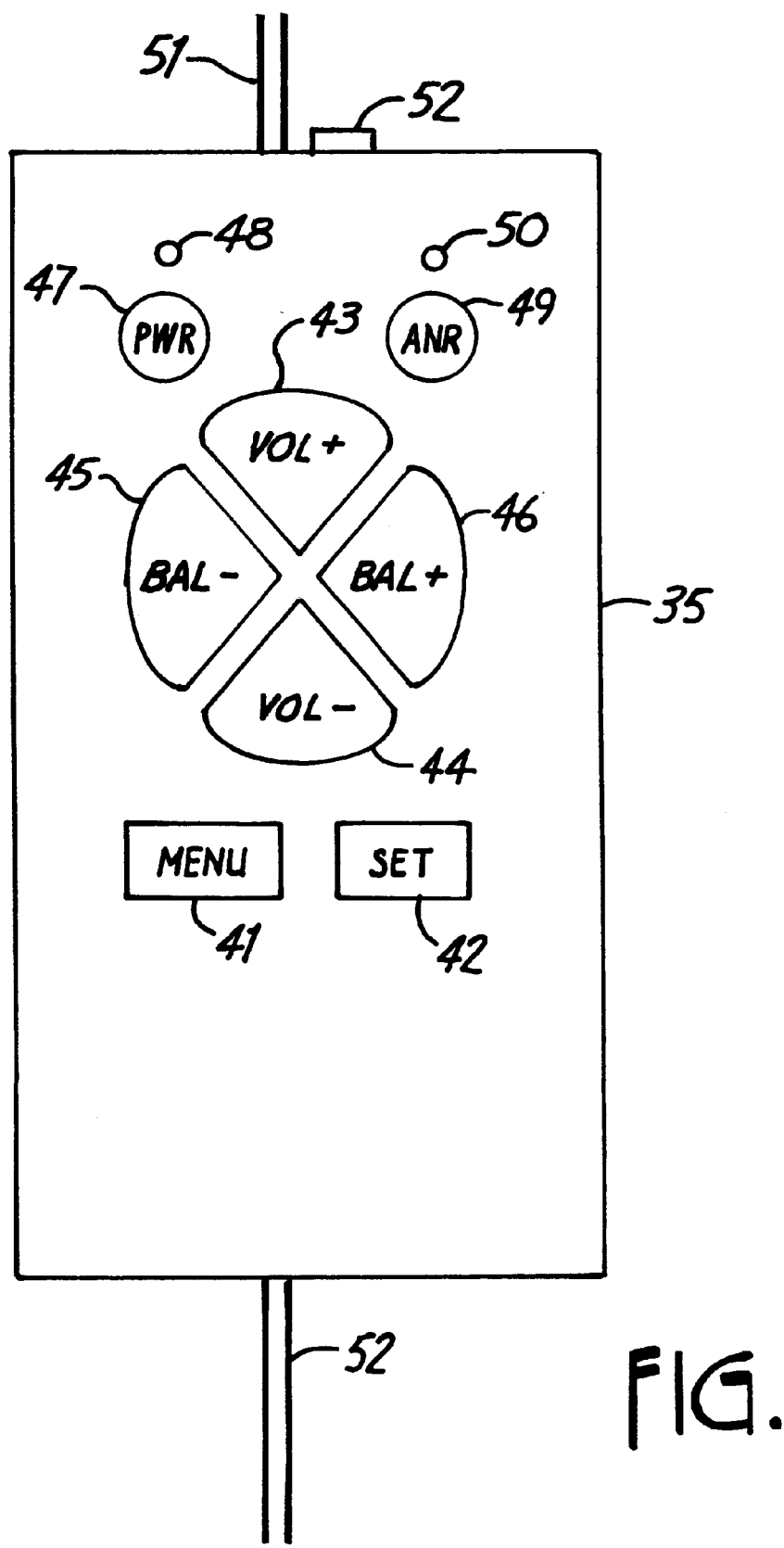
FIG. 9 illustrates a control housing that may be used in conjunction with a headset system of the invention.

Another advantage of employing a DSP in the headset system of the invention is the ease with which other signal processing features may be utilized. For example, FIG. 9 illustrates a housing 35 which contains the DSP and related electronic components. This housing 35 also includes a set of control switches, which can be activated by pressing the appropriate buttons shown in FIG. 9, for selecting special features. In a preferred embodiment, the DSP stores, in software, a series of menu items which the pilot can activate by pressing the "menu" button 41. The system will then successively issue audible options to the pilot, and the pilot can toggle those features on or off with the "set" button 42. Menu items could include features such as turning automatic volume control on/off (raising volume of the intercom or radio signal when the cabin is noisier, and lowering the volume when the cabin is quieter); enabling/disabling an automatic power off that turns the unit off after, e.g., five minutes without significant noise; enabling/disabling a low battery announcement; selecting between stereo and mono operation (and/or automatic detection of a stereo/mono signal); selecting bass or treble boost; selecting between a preset frequency response curve optimized for voice intelligibility and a preset frequency response curve optimized for music listening; announcing remaining battery life; announcing a measurement of the dB SPL of cockpit noise (e.g., as detected by an additional external microphone carried on the headset; etc.

The housing may also include volume up and down buttons 43 and 44, balance left and right buttons 45 and 46, a power button 47 (with accompanying indicator LED 48) and an on/off button 49 (with accompanying indicator LED 50) for the ANR feature of the system. A suitable cable 51 is provided for connecting the electronics contained in the housing 35 to the aircraft's intercom, and a similar cable 52 is provided to connect the electronics contained in the housing 35 to the headset. A jack 52 may also be provided for supplying external power to the unit when available (otherwise the unit is desirably powered by batteries contained within the housing 35). Though not shown in FIG. 9, the housing may also include a port or jack for connecting the DSP to a conventional port of a personal computer; software in the headset system can then easily be upgraded by the user by simply plugging the unit into the user's PC and running an update program supplied by the manufacturer.

While the invention has been described as implemented within a circumaural headset, it can also be utilized in connection with supra-aural headsets (i.e., headsets that are sometimes referred to as "lightweight" headsets, as they do not seal around the ear of the user, but, rather, sit on the outer ear). Such supra-aural headsets include those employing, e.g., gel-filled ear cushions, which seal against the outer ear, as well as those with foam ear cushions—though the foam ear cushions do not provide as much passive noise attenuation, the active noise cancellation system of the invention nevertheless would be effective for its purpose in such headsets. Also, the invention could be implemented in intra-aural devices, sometimes referred to as pilot earsets. Earsets have no headband and are inserted into the ear canal, usually supported by a hook resting around the pilot's outer ear. In such an implementation, if desired, a single transducer element can be used both as the speaker and the microphone.

While a preferred embodiment of the present invention has been described, it should be understood that various changes, adaptations and modifications may be made therein without departing from the spirit of the invention and the scope of the appended claims.

What is claimed is:

1. An active noise cancellation aircraft headset system comprising:

an earcup;

a speaker mounted within the earcup for receiving and acoustically transducing a composite noise cancellation signal;

a microphone mounted within the earcup for transducing acoustic pressure within the earcup to a corresponding analog error signal;

an analog filter which receives the analog error signal and inverts it to generate an analog broadband noise cancellation signal;

an analog to digital converter which receives the analog error signal and converts it to a digital error signal;

a digital signal processor which receives the digital error signal and, using an adaptive digital feedback filter, generates a digital tonal noise cancellation signal;

a digital to analog converter which converts the digital tonal noise cancellation signal to an analog tonal noise cancellation signal;

summing means for receiving and summing the analog broadband noise cancellation signal and the analog tonal noise cancellation signal to generate the composite cancellation signal, the summing means providing the composite noise cancellation signal to the speaker to at least partially cancel aircraft noise within the earcup.

2. The headset system of claim 1 further comprising a variable gain amplifier which amplifies the analog broadband noise cancellation signal, the gain of the variable gain amplifier being controlled by the digital signal processor.

3. The headset system of claim 1 wherein the digital tonal noise cancellation signal corresponds to a tonal noise generated by an aircraft engine.

4. The headset system of claim 1 wherein the digital signal processor is disposed within a housing external to the earcup.

5. The headset system of claim 4 further comprising a signal conductive cord connecting components mounted in the earcup to components carried in the housing, the cord having a disconnectable plug permitting the earcup to be disconnected from the housing.

6. The headset system of claim 4 further comprising:
one or more additional headsets each having:
an earcup;
a speaker mounted within the earcup for receiving and acoustically transducing a composite noise cancellation signal; and
a microphone mounted within the earcup for transducing acoustic pressure within the earcup to a corresponding analog error signal;
a signal conductive cord connecting each such headset to the housing;
an analog filter for each such additional headset, each such analog filter receiving the analog error signal for such headset and inverting it to generate an analog broadband noise cancellation signal for such headset;
analog to digital converter means for receiving the analog error signal for each such additional headset and converting it to a digital error signal for such headset;
the digital signal processor receiving the digital error signal for each such additional headset and, using the adaptive feedback filter, generating a digital tonal noise cancellation signal for such headset;
digital to analog converter means for converting the digital tonal noise cancellation signal for each such headset to an analog tonal noise cancellation signal for such headset;
summing means for receiving and summing the analog broadband noise cancellation signal for each such additional headset and the analog tonal noise cancellation signal for each such additional headset to generate the composite cancellation signal for each such additional headset, the summing means providing each respective composite noise cancellation signal to the speaker of the corresponding headset to at least partially cancel aircraft noise within the earcup of such headset.

7. The headset system of claim 1 wherein the digital signal processor is disposed within the earcup.

8. A method of canceling noise within an earcup of an aircraft headset, comprising the steps of:
transducing acoustic pressure within the earcup, which acoustic pressure includes both tonal noise generated by an engine of an aircraft and other broadband aircraft noise, to generate an analog error signal;
providing the analog error signal to an analog filter which inverts it and generates an analog broadband noise cancellation signal;
providing the analog error signal to an analog to digital converter which converts the analog error signal to a digital error signal;
providing the digital error signal to a digital signal processor and, using an adaptive feedback filter, generating a digital tonal noise cancellation signal;
providing the digital tonal noise cancellation signal to a digital to analog converter which converts the digital tonal noise cancellation signal to an analog tonal noise cancellation signal;
summing the analog broadband noise cancellation signal and the analog tonal noise cancellation signal to generate a composite cancellation signal, and providing the composite noise cancellation signal to a speaker within the headset earcup, the speaker acoustically transducing the composite cancellation signal to reduce aircraft noise within the earcup.

9. A method of canceling noise within an earcup of an aircraft headset, comprising the steps of:
transducing acoustic pressure within the earcup, which acoustic pressure includes both tonal noise generated by an engine of an aircraft and other broadband aircraft noise, to generate an analog error signal;
inverting the analog error signal to generate an analog broadband noise cancellation signal;
converting the analog error signal to a digital error signal;
using a digital signal processor employing an adaptive feedback filter to generate a digital tonal noise cancellation signal based on the digital error signal;
converting the digital tonal noise cancellation signal to an analog tonal noise cancellation signal;
summing the analog broadband noise cancellation signal and the analog tonal noise cancellation signal to generate a composite cancellation signal; and
acoustically transducing the composite cancellation signal within the headset earcup to reduce the tonal and broadband aircraft noise within the headset earcup.

10. An active noise cancellation aircraft headset system comprising:
an earset including means for receiving and acoustically transducing an electronic composite noise cancellation signal, and means for transducing acoustic pressure within the earset to a corresponding analog error signal;
an analog filter which receives the analog error signal and inverts it to generate an analog broadband noise cancellation signal;
an analog to digital converter which receives the analog error signal and converts it to a digital error signal;
a digital signal processor which receives the digital error signal and, using an adaptive feedback filter, generates a digital tonal noise cancellation signal;

a digital to analog converter which converts the digital tonal noise cancellation signal to an analog tonal noise cancellation signal;

summing means for receiving and summing the analog broadband noise cancellation signal and the analog tonal noise cancellation signal to generate the composite cancellation signal, the summing means providing the composite noise cancellation signal to the means for receiving and acoustically transducing the composite noise cancellation signal.

* * * * *